United States Patent [19]
Thimineur et al.

[11] Patent Number: 5,334,737
[45] Date of Patent: Aug. 2, 1994

[54] LIQUID SILICONE ESTERS

[75] Inventors: Raymond J. Thimineur, Scotia; Frank J. Traver, Troy; Virgina M. Van Valkenburgh, West Lebanon, all of N.Y.

[73] Assignee: General Electric Company, Waterford, N.Y.

[21] Appl. No.: 705,454

[22] Filed: May 24, 1991

[51] Int. Cl.$^5$ ............ C07F 7/08; C07F 7/18
[52] U.S. Cl. .................... 556/440; 556/437; 252/356; 424/59; 424/64; 424/65; 424/70; 424/78.03; 106/316; 8/115.6; 428/245; 428/266
[58] Field of Search ........ 556/440, 437; 252/356; 424/59, 64, 65, 70, 78.03; 106/316; 8/115.6; 428/245, 266

[56] References Cited

U.S. PATENT DOCUMENTS

| | | | |
|---|---|---|---|
| 3,112,333 | 11/1963 | Bailey | 260/448.2 |
| 4,568,566 | 4/1986 | Tolentino | 427/54.1 |
| 4,725,658 | 2/1988 | Thayer et al. | 528/15 |
| 5,049,617 | 9/1991 | Yoshioka et al. | 556/440 X |
| 5,098,981 | 3/1992 | Saho et al. | 556/440 X |
| 5,113,004 | 5/1992 | Yanagisawa et al. | 556/440 |

FOREIGN PATENT DOCUMENTS

| | | |
|---|---|---|
| 0229450 | 1/1989 | European Pat. Off. . |
| 0362860 | 4/1990 | European Pat. Off. . |
| 0363252 | 4/1990 | European Pat. Off. . |
| 0425121 | 5/1991 | European Pat. Off. . |

*Primary Examiner*—Paul F. Shaver

[57] ABSTRACT

The present invention provides a liquid silicone ester having a melting point of up to about 30° C., and comprising (A) units of the general formula $R_aR^E{}_bSiO_{[4-(a+b)]/2}$ or (B) $R_xR^E{}_ySiO_{\frac{1}{2}}$ units and $SiO_{4/2}$ units; $R^E$ being an ester-containing organic group. The silicone ester is liquid at ambient skin temperature and has improved workability, improved payout, improved emollient properties, greater solubility in organic compounds, greater substantivity to surfaces and improved water resistance.

15 Claims, No Drawings

LIQUID SILICONE ESTERS

BACKGROUND OF THE INVENTION

The present invention to silicone esters. More particularly, the present invention relates to liquid silicone esters which are useful in personal care products.

The usefulness of silicone ester waxes in personal care products is disclosed in U.S. Pat. No. 4,725,658 to Thayer et al (Thayer). These waxes have melt points which are higher than skin temperature, skin temperature being about 25° C.–30° C. Because the silicone esters disclosed in the Thayer patent are not liquid at skin temperature, they are generally hard, brittle materials which are difficult to work with and difficult to spread and apply.

It would be desirable therefore to provide a silicone ester having a melting point which is lower than skin temperature, i.e., less than 30° C., and, consequently, has improved workability and better payout, i.e., spreads out more readily on skin, hair, or other surfaces.

In addition, it would be desirable to provide a silicone ester having improved emollient properties and greater solubility in organic compounds.

It would further be desirable to provide a silicone ester having greater substantivity to surfaces and improved water resistance.

SUMMARY OF THE INVENTION

The present invention provides a silicone ester composition comprising a silicone ester or blend of silicone esters, the silicone ester or blend of silicone esters having a melting point of up to about 30° C., and comprising:

(A) units of the general formula:

$$R_a R^E_b SiO_{[4-(a+b)]/2} \quad (1)$$

wherein R is an organic radical, a is a number ranging from 0 to 3, b is a number ranging from 0 to 3, a+b is a number ranging from 1 to 3, with the proviso that there is present at least one $R^E$ radical, $R^E$ being an ester-containing organic group selected from the group consisting of:

(1)

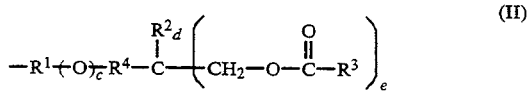

$$-R^1 \!\!\left(\!O\!\right)_{\!\!c}\!\! R^4\!\!-\!\!\overset{R^2_d}{\underset{}{C}}\!\!\left(\!CH_2\!-\!O\!-\!\overset{O}{\underset{}{C}}\!-\!R^3\!\right)_{\!\!e} \quad (II)$$

wherein c is 0 or 1; d is 0, 1, or 2; e is 1, 2, or 3; the sum of d+e being 3; further wherein $R^1$ is a linear or branched organic group having from 2 to about 14 carbon atoms if the ester-containing organic group (1) contains no olefinic unsaturation and $R^1$ is a linear or branched organic group having from about 2 to about 18 carbon atoms if the ester-containing organic group (1) contains olefinic unsaturation; further wherein $R^2$ is hydrogen or an organic radical of from 1 to about 6 carbon atoms; $R^3$ is a linear unsaturated organic radical of from 1 to about 23 carbon atoms, a linear saturated organic radical of from 1 to about 17 carbon atoms, or a branched organic radical of from about 1 to about 35 carbon atoms; and $R^4$ is a linear or branched organic radical having 0 to about 6 carbon atoms;

(2)

$$-R^5\!-\!\overset{O}{\underset{}{C}}\!-\!O\!-\!\overset{R^6}{\underset{R^8}{C}}\!-\!R^7 \quad (III)$$

wherein $R^5$ is a linear or branched organic group having from 2 to about 15 carbon atoms if the ester-containing organic group (2) contains no olefinic unsaturation and $R^5$ is a linear or branched organic group having from 2 to about 23 carbon atoms if the ester-containing organic group (2) contains olefinic unsaturation; further wherein $R^6$ is hydrogen or a linear or branched organic radical of from 1 to about 6 carbon atoms, and $R^7$ is a linear unsaturated organic radical of from 1 to about 23 carbon atoms, a linear saturated organic radical of from 1 to about 17 carbon atoms, or a branched organic radical of from 1 to about 35 carbon atoms; and $R^8$ is hydrogen or a linear or branched organic group having from 1 to about 6 carbon atoms;

or (3)

$$-R^9\!-\!O\!-\!\overset{O}{\underset{}{C}}\!-\!\overset{R^{11}}{\underset{R^{12}}{C}}\!-\!R^{10} \quad (IV)$$

wherein $R^9$ is a linear or branched organic group having from 2 to about 14 carbon atoms if the ester-containing organic group (3) contains no olefinic unsaturation and $R^9$ is a linear or branched organic group having from 2 to about 24 carbon atoms if the ester-containing organic group (3) contains olefinic unsaturation; $R^{10}$ is a linear unsaturated organic radical of from 1 to about 22 carbon atoms, a linear saturated organic radical of from 1 to about 14 carbon atoms, or a branched organic radical of from 1 to about 34 carbon atoms; $R^{11}$ is hydrogen or a linear or branched organic radical of from 1 to about 6 carbon atoms; and $R^{12}$ is hydrogen or a linear or branched organic radical of from 1 to about 6 carbon atoms; or (4) chemical reaction mixtures of (1), (2), and (3); or (B) $R^{13}_x R^E_y SiO_{\frac{1}{2}}$ units and $SiO_{4/2}$ units;

wherein each $R^{13}$ is independently an organic radical, x is a number ranging from 0 to 3, y is a number ranging from 0 to 3, x+y is 3, with the proviso that there is present at least one $R^E$ radical, $R^E$ being an ester-containing organic group as defined in (A); the ratio of $R^{13}_x R^E_y SiO_{\frac{1}{2}}$ units to $SiO_{4/2}$ units being from about 0.5:1 to about 4:1.

The present invention is further directed to physical mixtures and chemical mixtures of the foregoing silicone ester liquids and to personal care or textile softening compositions containing the liquid silicone esters or mixtures thereof. The invention is further directed to methods for improving the substantivity, payout, and workability of personal care compositions by incorporating therein the silicone esters or mixtures of the silicone esters of this invention.

The liquid silicone esters of the present invention have greater substantivity to surfaces, improved water resistance, improved workability, greater payout on surfaces, improved emollient properties and greater solubility in organic compounds.

DETAILED DESCRIPTION OF THE INVENTION

The present invention is directed to silicone esters which are liquid at skin temperature or below. The silicone esters of this invention have a melting point of up to about 30° C. and preferably up to about 25° C.

The liquid silicone esters of this invention are selected from (A) silicone esters having units of the general formula $$R_a R^E_b SiO_{[4-(a+b)/2]} \quad (1)$$

or (B) silicone esters having units of the general formulae:

$$R^{13}_x R^E_y SiO_{\frac{1}{2}} \text{ units and } SiO_{4/2} \text{ units.} \quad (1)$$

In formulas (I) and (V), R and $R^{13}$ are each independently an organic radical; $R^E$ is an ester-containing organic radical as described hereinabove; a is a number of from 0 to 3; b is a number of from 0 to 3; the sum of a+b is a number of from 1 to 3; x is a number of from 0 to 3; y is a number of from 0 to 3; and the sum of x+y is 3.

In formula (II), the ratio of $R^{13}_x R^E_y SiO_{\frac{1}{2}}$ units to $SiO_{4/2}$ units is from about 0.5:1 to about 4:1 and preferably from about 1:1 to about 3:1.

In formulas (I) and (V), radicals represented by R and $R^{13}$ include any substituted or unsubstituted organic radical, for example, alkyl radicals, such as methyl, ethyl, propyl, hexyl, octyl, decyl, cyclohexyl, cycloheptyl, and the like; aryl radicals such as phenyl, tolyl, xylyl, naphthyl, and the like; aralkyl radicals such as phenylethyl, benzyl, and the like; or any of the foregoing wherein one or more hydrogen atoms is replaced with, for example, a halogen, cyano, amino, or the like. Most preferably, all of the R and $R^{13}$ radicals are methyl or a mixture of methyl and phenyl.

As mentioned above, the silicone esters of this invention must contain at least one $R^E$ radical. $R^E$ is an ester-containing organic radical selected from the group consisting of the radical represented by Formulas (II)–(IV) above.

In the ester-containing radical of Formula (II), c preferably represents 1, d preferably represents 1, and e preferably represents 2.

The number of carbon atoms in each of the $R^1$–$R^{12}$ radicals and the branched or linear nature of the ester-containing radicals are critical to the melting point of the silicone ester, and, accordingly, to whether the silicone ester is a liquid at skin temperature.

The $R^1$–$R^{12}$ radicals represent both saturated and unsaturated organic radicals. Preferably, the $R^1$–$R^{12}$ radicals represent linear or branched alkyl or alkenyl radicals containing the number of carbon atoms recited above.

The number of carbon atoms required in the radicals represented by the $R^1$, $R^3$, $R^5$, $R^7$, $R^9$, and $R^{11}$ radicals in order to provide a silicone ester which is liquid at skin temperature in turn depends on the level of olefinic unsaturation in the ester-containing radical.

Thus, $R^1$, $R^5$, and $R^9$ are linear or branched organic groups, preferably alkyl groups, having from about 2 to about 14, preferably from about 2 to about 12, and most preferably from about 3 to about 10, carbon atoms if the ester-containing organic groups (1), (2), and (3), respectively, contain no olefinic unsaturation and $R^1$, $R^5$, and $R^9$ are linear or branched organic groups having from about 2 to about 18, preferably from about 2 to about 16, and most preferably, from about 3 to about 10 carbon atoms if the ester-containing organic groups (1), (2), and (3), respectively, contains olefinic unsaturation.

Typically, the ester-containing organic radicals of formulas (1)–(3) will have up to about 2 mole percent of olefinic unsaturation.

$R^2$ is hydrogen or a linear or branched organic group, preferably an alkyl group, having from 1 to about 6, preferably from about 1 to about 5, and most preferably from about 1 to about 3, carbon atoms.

$R^3$ is a linear or branched organic group, preferably an alkyl group, having from 1 to about 35, preferably from about 8 to about 25, and most preferably from about 11 to about 17, carbon atoms.

$R^4$ is linear or branched organic group, preferably an alkyl group, having from 0 to about 6, preferably from about 1 to about 5, and most preferably from about 1 to about 3 carbon atoms.

$R^6$ is hydrogen or a linear or branched organic group. The preferred organic groups represented by $R^6$ are alkyl groups having from 1 to about 6, preferably from about 1 to about 5, and most preferably from about 1 to about 3 carbon atoms. Preferably, $R^6$ is hydrogen.

$R^7$ is a linear or branched organic group, preferably an alkyl group, having from 1 to about 35, preferably from about 8 to about 25, and most preferably from about 11 to about 17, carbon atoms.

$R^8$ is hydrogen or a linear or branched organic group. $R^8$ is preferably an alkyl group having from 1 to about 6, preferably from about 1 to about 5, and most preferably from about 1 to about 3, carbon atoms.

$R^{10}$ is a linear or branched organic group, preferably an alkyl group, having from 1 to about 34, preferably from about 8 to about 25, and most preferably from about 10 to about 16, carbon atoms.

$R^{11}$ is hydrogen or a linear or branched organic group. The preferred organic groups represented by $R^{11}$ are alkyl groups having from 1 to about 6, preferably from about 1 to about 5, and most preferably from about 1 to about 3, carbon atoms. Most preferably, $R^{11}$ is hydrogen.

$R^{12}$ is hydrogen or a linear or branched organic group, preferably an alkyl group, having from 1 to about 6, preferably from about 1 to about 5, and most preferably from about 1 to about 3, carbon atoms.

Examples of preferred silicone esters within the scope of the present invention include silicone ester resins of the general formula $M'_2Q$, wherein Q represents $SiO_{4/2}$ units and M' represents $R^E(CH_3)_2SiO_{3/2}$ units, wherein $R^E$ is as defined above. Also preferred are linear silicone esters of the formula:

$$(CH_3)_3SiO[R^E(CH_3)SiO]_v[(CH_3)_2SiO]_wSi(CH_3)_3 \quad (VI)$$

wherein v represents a number from 1.0 to 25, w represents a number from 0 to 100, and $R^E$ is as defined previously herein.

Examples of preferred radicals represented by $R^E$ include:

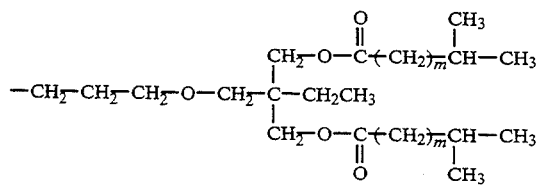
(VII)

wherein m is a number ranging from about 8 to about 14;

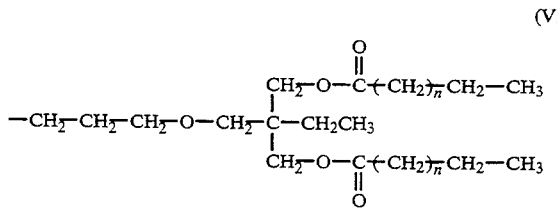
(VIII)

wherein n is a number ranging from about 9 to about 13;

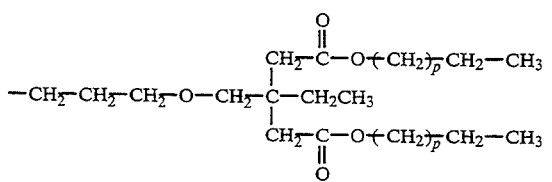
(IX)

wherein p is a number ranging from about 10 to about 14;

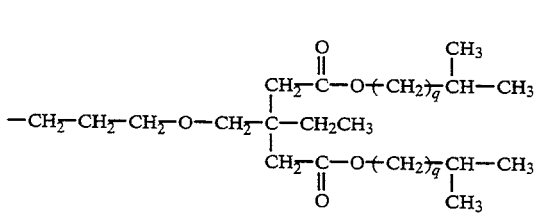
(X)

wherein q is a number ranging from about 9 to about 15;

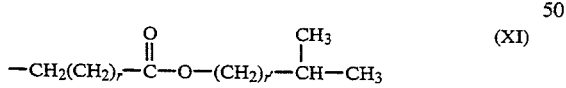
(XI)

wherein r is a number ranging from about 3 to about 9 and r' is a number ranging from about 9 to about 15;

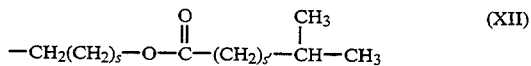
(XII)

wherein s is a number in the range of from about 2 to about 10 and s' is a number in the range of from about 8 to about 14;

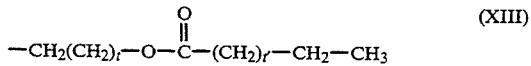
(XIII)

wherein t is a number in the range of from about 2 to about 10 and t' is a number in the range of from about 9 to about 13;
or

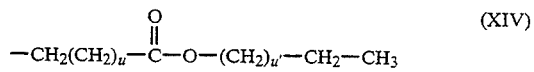
(XIV)

wherein u is a number in the range of from about 3 to about 9 and u' is a number in the range of from about 9 to about 14.

The present invention is further directed to compositions containing physical mixtures, i.e., blends, of the foregoing novel silicone ester liquids. The physical mixtures are prepared by mixing the various components at or above the melting point of all the ingredients to be used in the blend.

As mentioned hereinabove, the silicone ester of this invention has a melting point of up to about 30° C. and preferably up to about 25° C. It has been found that the melting point can be as low as −60° C. and even as low as −100° C. when branched silicone esters are used.

The liquid silicone esters of this invention can be prepared from organohydrogenpolysiloxanes and alcohol esters of fatty acids having terminal olefinic unsaturation.

Thus, prior to reaction with an organohydrogenpolysiloxane, $R^E$ in formulas (I) and (V) above can be represented, for example, by the general formulas:

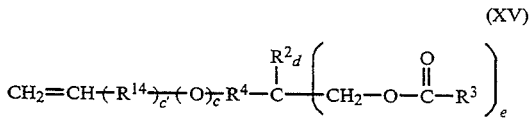
(XV)

wherein $R^{14}$ is an organic radical, preferably an alkylene or branched alkylene radical, having from 1 to about 12 carbon atoms if the compound of formula (XV) contains no olefinic unsaturation and from 1 to about 16 carbon atoms if the compound of formula (XV) contains olefinic unsaturation; c' is 0 or 1; and $R^2$, $R^3$, d, $R^4$, and e are as previously defined;

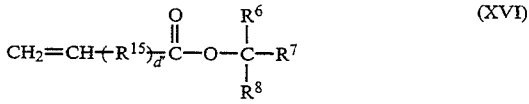
(XVI)

wherein $R^{15}$ is an organic radical, preferably an alkylene or branched alkylene radical, having from 0 to about 12 carbon atoms if the compound of formula (XVI) contains no olefinic unsaturation and from 0 to about 16 carbon atoms if the compound of formula (XVI) contains olefinic unsaturation; d' is 0 or 1; and $R^5$, $R^6$, and $R^7$ are as previously defined;

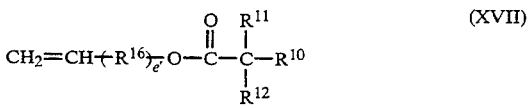
(XVII)

wherein $R^{16}$ is an organic radical, preferably an alkylene or branched alkylene radical, having from 0 to about 12 carbon atoms if the compound of formula (XVII) contains no olefinic unsaturation and from 0 to about 16 carbon atoms if the compound of formula (XVII) contains olefinic unsaturation; e' is 0 or 1; and $R^{10}$, $R^{11}$, and $R^{12}$ are as previously defined;

The olefinic esters of formulas (XV)–(XVII) can be prepared by reacting an alcohol with a carboxylic acid having terminal olefinic unsaturation, or, alternatively, by reacting an alcohol having terminal olefinic unsaturation with a carboxylic acid. The alcohol and the acid may be branched or linear, or one may be branched and the other linear.

Examples of alcohols suitable for making the liquid silicone esters of this invention include trimethylolpropane monoallylether (TMPMAE), stearyl alcohol, and octyl alcohol. Trimethylolpropane monoallylether is preferred. Examples of suitable acids for making the liquid silicone esters of this invention include palmitic acid, myristic acid, lauric acid, isostearic acid, and undecylenic acid. Lauric acid and isostearic acid are preferred.

It should be understood that $R^E$, prior to reaction with organohydrogenpolysiloxane, must contain the number of carbon atoms recited above so as to impart a liquid consistency to the composition of formulas (I) and (II) and must also contain terminal olefinic unsaturation. The terminal olefinic unsaturation allows the organic ester (i.e. $R^E$) to be added to the organohydrogenpolysiloxane in the presence of a hydrosilation catalyst.

The organohydrogenpolysiloxanes useful for making the silicone esters of this invention may be linear or resinous. The linear organohydrogenpolysiloxane polymers preferably have the formula

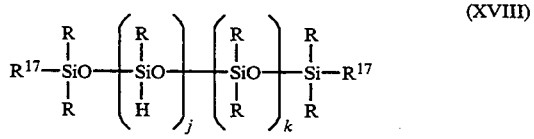
(XVIII)

wherein R is as previously defined herein, $R^{17}$ is hydrogen or R, and j and k vary such that the polymer has a viscosity of from about 5 to about 1000 centipoise at 25° C., with the proviso that if v equals zero, $R^{17}$ is hydrogen. Such linear hydride polymers preferably have from about 10 to 100 mole percent Si-H containing siloxy units.

The preferred organohydrogenpolysiloxane resins comprise

(XIX)

and $SiO_{4/2}$ units, where the sum of R and H groups per silicon atom varies from 1.0 to 3.0. Such resins may also include a limited number of difunctional units.

The most preferred organohydrogensiloxanes for use in this invention are hydrogen siloxane resins containing $(H)(CH_3)_2SiO_{\frac{1}{2}}$ units ("$M^H$" units) and $SiO_{4/2}$ units ("Q" units), wherein the ratio of $M^H$ units to Q units is from about 0.6:1 to about 4:1, preferably 2:1t.

These and other suitable organohydrogenpolysiloxanes are well known in the art, for example, as described in U.S. Pat. Nos. 3,344,111 and 3,436,366, both of which are incorporated by reference into the present disclosure.

Suitable hydrosilation catalysts are well known in the art, for example, platinum-containing catalysts as described in U.S. Pat. Nos. 3,159,601; 3,159,662; 3,220,970; 3,516,946; and 3,814,730, all of which are incorporated by reference into the present disclosure. Other suitable hydrosilation catalysts can be based on the metals rhodium, ruthenium, palladium, osmium, iridium, and platinum. Generally, the olefinically unsaturated ester can be added to the organohydrogenpolysiloxane in the presence of from about 10 to about 500 ppm of catalyst, based on the metal.

The silicone esters of the present invention are useful in personal care compositions. Examples of personal care products which may contain the silicone ester compositions of this invention include lipsticks, eyeshadows, bronzes, blushes, lotions, handcreams, antiperspirants, shampoos, hair conditioners, an emollient, an antiseptic, a sunscreen agent, a cleansing agent, hair styling products, hair sprays, spritzes, and other skin care and hair care products.

The silicone esters and silicone ester compositions of the present invention may also be used to soften textile materials. Textile fabrics suitable for treatment with the composition of this invention include, for example, polyester, polyester cotton, polyester rayon, cotton, rayon, nylon, and the like.

Typically, the novel esters of this invention are used in a silicone-water emulsion which is in turn used as a vehicle for the application of personal care agents or textile-softening agents. The silicone-water emulsion may be either water-in-oil or oil-in-water type emulsions.

Thus, another embodiment of this invention is a water-in-oil type of emulsion wherein the silicone-water emulsion composition of this invention comprises by weight:

(a) from about 10 to about 70 parts of the liquid silicone ester or mixtures of liquid silicone esters of this invention as a continuous phase;

(b) from about 0.25 to about 10 parts of an emulsifier; and (c) from about 20 to about 89.75 parts of water as a dispersed phase, wherein the sum of (a), (b), and (c) is 100 parts.

Another embodiment is an oil-in-water emulsion wherein the silicone-emulsion of this invention comprises by weight:

(a) from about 0.1 to about 60 parts of the liquid silicone ester or mixtures of liquid silicone esters of this invention as a continuous phase;

(b) from about 0.25 to about 10 parts of an emulsifier; and (c) from about 30 to about 99.65 parts of water as a dispersed phase, wherein the sum of (a), (b), and (c) is 100 parts.

The silicone-water emulsion compositions of this invention may further comprise polar materials such as those disclosed, for example, in U.S. Pat. No. 4,122,029 (Gee et al.), which is hereby incorporated by reference herein. Suitable polar liquids include water, salts, weak acids, weak bases and aqueous solutions thereof and organic materials bearing polar groups. Emulsion compositions comprising water and/or ethanol are particularly useful.

The silicone-water emulsion composition above may be combined with (d) an effective amount of a personal care agent or a textile softening agent. The term "personal care agent" as used herein refers to an additive of a cosmetic or medicinal nature which is generally regarded as providing beneficial results when applied externally to the skin of a user. Effective amounts of a personal care agent typically range from about 0.1 to 20,000 parts by weight of the personal care agent per 100 parts of the emulsion. Effective amounts of a textile softening agent typically range from about 0.1 to 5 parts by weight of the textile softening agent per 100 parts of the emulsion.

Polar materials of particular interest for the composition of this invention are therefore selected from the group consisting of water, water solutions of polar solutes, polar liquids soluble in water. Suitable water solutions comprise, as the polar solute, inorganic solutes and organic solutes such as sorbitan, alcohols, e.g., glycerine and polyether glycols; nitrogen compounds such as amides, nitriles, and amines; acids; and ethers.

The emulsifying agents used in the personal care or textile softening compositions of this invention may be nonionic, anionic, cationic, or amphoteric but of particular importance are those classes of nonionic emulsifiers which are highly ethoxylated. The ethoxylated fatty acids, ethoxylated and nonethoxylated sorbitan esters, ethoxylated alkyl phenols, and ethoxylated ethers provide the best results.

Examples of suitable emulsifiers for use in the personal care or textile-softening compositions of this invention include those disclosed in U.S. Pat. No. 4,784,844 (Thimineur et al.), which is hereby incorporated by reference herein. The preferred emulsifier for use in the water-in-oil emulsion composition of this invention is a mixture of polysorbate 80 and a silicone polyether copolymer in a cyclics mixture of decamethylcyclopentasiloxane and octamethylcyclotetrasiloxane, the silicone polyether copolymer in cyclics mixture having a viscosity of 3000 centipoise at 25° C. and a solids content of 9–11%. The preferred emulsifier for use in the oil-in-water emulsion composition of this invention is DEA-cetylphosphate, wherein DEA represents diethanolamine.

The order of mixing of (a)–(d) is not critical, however, particularly satisfactory results can be obtained when the emulsifying agent and the water are mixed together in preblend to which the liquid silicone ester is added. The personal care agent or the textile-treating agent are then added to the resulting composition.

The silicone-water emulsion can be made in the form of a lotion as well as a paste or cream-like consistency and can be made further viscous in the form of an ointment, salve, or gel.

The preblended water-emulsifier mixture is provided by stirring with moderate heat until a uniform blend is obtained whereupon the liquid silicone ester is added and mixed slowly.

Skin may be treated by the ester compositions of this invention by simply applying the ester composition to the surface of the skin. In treating hair, the ester or composition is applied to the surface of the hair in any suitable manner such as by massaging the composition throughout the hair by hand, by dipping the hair into the composition, or by brushing or combining the ester or composition throughout the hair or by spraying.

In softening textile with the composition of this invention, the composition is applied to at least one surface of the textile fabric in any suitable manner such as by dipping, spraying, or brushing. The applied liquid composition is then heated to a temperature of from above room temperature to less than the melting or decomposition temperature of the textile fabric. Heating can be done by any suitable method or combination of methods, but preferably is done by passing the coated textile through a hot air oven. The coated fabric should be heated for an amount of time sufficient to evaporate any water that is present.

Another embodiment of the present invention is a method for improving the substantivity, water resistance, workability, emollient properties, payout, and solubility in organic compounds of a personal care or textile softening composition, comprising the step of combining the personal care or textile softening composition with an effective amount of the liquid silicone ester of this invention or chemical or physical mixtures of the liquid silicone esters of this invention.

The present invention is also directed to articles comprising a substrate coated with a silicone ester within the scope of this invention or chemical mixtures or physical mixtures of the silicone esters of this invention, or with the personal care or textile softening compositions of this invention. The substrate is preferably skin, hair, plastic, or textile material.

In order to better able the artisan to practice the present invention, the following examples are provided by way of illustration and not by way of limitation. All parts and percentages are by weight unless otherwise noted.

EXPERIMENTAL

EXAMPLE 1

Example 1 illustrates the preparation of a liquid silicone ester within the scope of the present invention.

To a one liter round bottom flask equipped with stirrer, thermometer, and reflux head, there was added 47.43 parts of 95% myristic acid, 19.00 parts of trimethylol propane monoallyl ether (TMPMAE), 0.37 part of p-toluene sulfonic acid as catalyst, and 33.20 parts of a toluene solvent. The mixture was heated to 110°–120° C. and held there for 4–8 hours, during which time water was removed from the toluene/water azeotrope and the esterification driven to completion. Infrared spectroscopy indicated deletion of the organic acid peak and the presence of the ester. Once the reaction was complete, the p-toluene sulfonic acid catalyst was neutralized with sodium bicarbonate. The resultant ester had a solids content of about 65%.

A platinum-containing catalyst solution (0.029 parts) prepared by reacting octyl alcohol and chloroplatinic acid was then added to the ester prepared above and the resulting mixture was warmed to 120° C. at which time about 10.70 parts of a hydrogen-containing siloxane resinous copolymer containing $(CH_3)_2SiO_{\frac{1}{2}}$ units ("M" units) and $SiO_{4/2}$ units ("Q" units) and having a hydrogen content of 0.8 to 1.2% was added. The mixture was heated at reflux until all of the SiH was consumed, as determined by IR analysis. The resultant liquid silicone ester was stripped under vacuum to remove toluene and thereafter filtered while hot through Celite #545 to improve the ester's appearance. The resultant ester product had a solids content of about 100%, a hydrogen content of about 0.01, and a melting point of +5° C. +/− 2° C.

EXAMPLES 2–9

Eight liquid silicone esters were prepared as described in Example 1 except that the organic acid, organic alcohol, and organohydrogensiloxane used in the preparation of the esters varied as shown in Table 1 below. The freezing points of the esters prepared in Examples 2-9 are shown in Table 2. These examples illustrate that the esters used in the present invention are liquid at ambient skin temperature.

In Table 1, the term "TMPMAE" represents trimethylol propane monoallyl ether; "$M^HQ$" represents a hydrogen siloxane resin containing $(H)(CH_3)_2SiO_{\frac{1}{2}}$ units and $SiO_{4/2}$ units, and having a hydrogen content of about 0.8-1.2 weight %; and "SiH Fluid" represents a methylhydrogen siloxane fluid having a hydrogen content of 0.72-1.00 weight % and a viscosity of approximately 35-75 centistokes at 25° C.

TABLE 1

| Examples 2-9: Starting Materials | | | |
|---|---|---|---|
| Example No. | Organic Acid | Organic Alcohol | Organohydrogensiloxane |
| 2 | Stearic Acid | TMPMAE | $M^HQ$ |
| 3 | Palmitic Acid | TMPMAE | $M^HQ$ |
| 4 | Myristic Acid | TMPMAE | $M^HQ$ |
| 5 | Lauric Acid | TMPMAE | $M^HQ$ |
| 6 | Undecylenic Acid | Stearic | $M^HQ$ |
| 7 | Undecylenic Acid | Octyl | $M^HQ$ |
| 8 | Stearic Acid | TMPMAE | SiH Fluid |
| 9 | Isostearic Acid | TMPMAE | $M^HQ$ |

TABLE 2

| Examples 2-9: Freezing Points | |
|---|---|
| Example No. | Freezing Point |
| 2 | 32° C. |
| 3 | 18° C. |
| 4 | +5° C. |
| 5 | −25° C. |
| 6 | 31° C. |
| 7 | 12° C. |
| 8 | 23° C. |
| 9 | less than −45° C. |

Example 10 and Comparison Examples A-D

In Example 10 and Comparison Examples A-D, the substantivity and water resistance of the liquid silicone ester prepared in Example 4 (represented as Example 10 in Table 3 below) was compared to the substantivity and water resistance of a polydimethylsiloxane fluid having a viscosity of 350 centistokes at 25° C. (Comparison Example A), a siloxane resin containing $(CH_3)_3SiO_{\frac{1}{2}}$ units ("M" units) and $SiO_{4/2}$ units ("Q" units) in polydimethylsiloxane fluid having a viscosity of 50 centistokes (Comparison Example B, isopropyl palmatate (Comparison Example C), and myristyl propionate (Comparison Example D). The substantivity and water resistance properties of these materials were measured by placing side-by-side films of the materials onto a clear polycarbonate substrate and then evaluating the amount of film of each material remaining on the substrate after 5 successive sprays of the films with 250 ml aliquots of water.

The results are shown in Table 3.

TABLE 3

| Example 10 and Comparison Examples A-D: Substantivity and Water Resistance Properties | | | | | |
|---|---|---|---|---|---|
| | % of Film Remaining | | | | |
| Example No. | Aliquot No. 1 | Aliquot No. 2 | Aliquot No. 3 | Aliquot No. 4 | Aliquot No. 5 |
| 10 | 100 | 75-90 | 50 | 50 | 25 |
| Comp. A | 0 | — | — | — | — |
| Comp. B | 50 | 25 | 0 | 0 | — |
| Comp. C | 0 | — | — | — | — |
| Comp. D | 25 | 0 | — | — | — |

In Table 3 above, the "—" indicates that no film remained on the substrate.

The results shown in Table 3 indicate that the liquid silicone esters of the present invention have better substantivity and water resistance properties on plastic surfaces than other silicone and organic esters commonly used in personal care products.

Example 11 and Comparative Examples E and F

Example 11 and Comparative Examples E and F illustrate the substantivity to skin of the liquid silicone ester of the present invention. In Example 11, skin is treated with the silicone ester liquid of the present invention; in Comparative Example E, the skin was treated with myristyl propionate; and in Comparative Example F, the skin was left untreated.

Three 5 cm² areas of smooth shaved arm skin were selected and isolated. Each skin section was washed with soap and water and then wiped with isopropyl alcohol to remove soap and residual oil from the skin. The skin section in Example 11 was then treated with 1 gram of the liquid silicone ester prepared in Example 4 which was uniformly spread on the skin section. The skin section in Comparison Example E was treated with 1 gram of myristyl propionate uniformly spread on the surface of the skin. In Comparison Example F, the skin section was left untreated. The skin sections were then immersed in warm water (having a temperature of about 30°-35° C.) for about 40 minutes with mild movement. The treated skin sections were then allowed to dry.

After drying, each skin section was marked with a yellow felt marker pen and wiped with a soft absorbent tissue. The skin section treated with the liquid silicone ester (Example 11) was wiped clean of the yellow marking, whereas the section treated with myristyl propionate (Comparison Example E) and the untreated skin section (Comparison Example F) both retained the yellow marking. After washing with mild soap and water, the myristyl propionate-treated and untreated skin sections still had visible yellow markings.

The results obtained in Example 11 and Comparison Examples E and F indicate that the liquid silicone ester of the present invention remained on the treated skin in an amount sufficient to prevent the yellow dye from reaching the base skin surface whereas either no amount or an insufficient amount of myristyl propionate remained on the treated skin to prevent the dye from reaching the base skin.

Example 12 and Comparison Examples G and H

Three compositions having the formulations shown in Table 4 below were prepared. The term "SF-I" in Table 4 refers to a silicone polyether copolymer in a cyclics mixture of decamethylcyclopentasiloxane and octamethylcyclotetrasiloxane and having a viscosity of 3000 centipoise at 25° C. and a solids content of 9–11%. The term "SF-II" in Table 4 refers to a silicone volatile fluid decamethylcyclopentasiloxane.

TABLE 4

Example 12 and Comparison Examples G and H: Formulations

| Ingredient | Example 12 | Comparative Example G | Comparative Example H |
|---|---|---|---|
| Part A Amount (parts by weight) | | | |
| SF-I | 10.0 | 10.0 | 10.0 |
| Liquid Silicone Ester | 5.0 | 0 | 0 |
| SF-II | 10.0 | 10.0 | 10.0 |
| Myristyl Propionate | 0 | 0 | 5.0 |
| Part B Amount (parts by weight) | | | |
| Polysorbate 80 | 0.2 | 0.2 | 0.2 |
| Glycerine | 3.0 | 3.0 | 3.0 |
| Water | 70.8 | 75.8 | 70.8 |
| NaCl | 1.0 | 1.0 | 1.0 |

The compositions shown in Table 4 above were prepared by adding Part B to Part A with high shear agitation and then milling the resulting blend for 1 minute in a homogenizer.

Three 5 cm² areas of smooth shaved arm skin were prepared as described in Example 11 and Comparison Examples E and F above. The skins sections were each washed with soap and water and dried, and then wiped with isopropyl alcohol. One skin section was then treated with the composition of Example 12, a second section was treated with the composition of Comparison Example G and a third section was treated with the composition of Comparison Example H. The skin sections were then immersed in warm water (having a temperature of about 30°–35° C.) for about 40 minutes with mild movement.

A yellow felt marking pen was then applied to each of the treated skin sections as described in Example 9 and Comparison Examples E and F. The skin section treated by the composition containing the liquid silicone ester (Example 12) was the only one from which the mark was completely removed by tissue after washing with soap and water.

Example 12 and Comparative Examples G and H show that the liquid silicone esters of the present invention have greater substantivity and water resistance than other silicone and organic esters commonly used in personal care products.

Example 13 and Comparative Example I

Two compositions having the formulations shown in Table 5 below were prepared.

TABLE 5

Example 13 and Comparative Example I: Formulations

| Ingredients | Example 13 | Comparative Example I |
|---|---|---|
| PART A | | |
| Stearic Acid | 3.00 | 3.00 |
| Cetyl Alcohol | 2.00 | 2.00 |
| DEA-Cetylphosphate | 2.50 | 2.50 |
| Octyldimethyl PABA | 7.50 | 7.50 |
| Octyl Salicylate | 5.00 | 5.00 |
| SF-II | 5.00 | 5.00 |
| Liquid Silicone Ester | 7.00 | — |
| Isopropyl Myristate | — | 7.00 |
| PART B | | |
| Glycerine | 4.00 | 4.00 |
| Dowacil 200 | 0.10 | 0.10 |
| Keltrol T | 0.35 | 0.35 |
| Water | 63.55 | 63.55 |

The compositions of Example 13 and Comparison Example I were prepared by heating Part A and Part B to 85°–90° C. Part A was then added to Part B with high shear agitation and the resulting mixture was cooled.

Substantivity and water resistance properties of the compositions prepared in Example 13 and Comparison Example I were measured by placing side-by-side films of the compositions on a panel of polycarbonate substrate and then subjecting the films to six successive sprays of 250 ml aliquots of water. The results are shown in Table 6.

TABLE 6

Example 13 and Comparative Example I: Substantivity and Water Resistance Properties

| Example No. | % of Film Remaining After Spray | | | | | |
|---|---|---|---|---|---|---|
| | After 1st spray | After 2nd spray | After 3rd spray | After 4th spray | After 5th spray | After 6th spray |
| 13 | 100 | 100 | 75–90 | 50 | 50 | 25 |
| Comparison Example I | 75–90 | 50 | 25 | * | — | — |

*slight haze remained but no observable film

The results shown in Table 6 indicate that the composition containing the liquid silicone ester (Example 13) has better substantivity and water resistance than the composition containing isopropyl myristate.

EXAMPLE 14

Example 14 illustrates the preparation of a liquid silicone ester using branched fatty acids.

A liquid silicone ester was prepared by reacting 2 equivalents of isostearic acid with 1 equivalent of trimethylolpropane monoallylether (TMPMAE) and then reacting the resulting ester in a hydrosilation reaction with a hydrogen-containing siloxane resinous copolymer containing $(CH_3)_2HSiO_{\frac{1}{2}}$ units (M units) and $SiO_{4/2}$ units (Q units). The resulting branched silicone ester is a liquid.

What is claimed is:

1. A silicone ester composition comprising a liquid silicone ester or blend of silicone liquid esters, the silicone liquid ester or blend of silicone liquid esters having a freezing point of up to about 30° C., and comprising:
(A) units of the general formula:

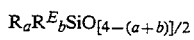
(1)

wherein R is an organic radical, a is a number ranging from 0 to 3, b is a number ranging from 0 to 3, a+b is a number ranging from 1 to 3, with the proviso that there is present at least one $R^E$ radical, $R^E$ being an ester-containing organic group selected from the group consisting of:

(1)

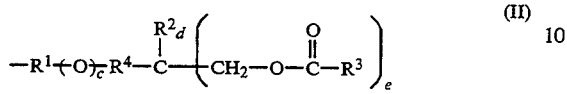

(II)

wherein c is 0 or 1; d is 0, 1, or 2; e is 1, 2, or 3; the sum of d+e being 3; further wherein $R^1$ is a linear or branched organic group having from 2 to about 14 carbon atoms if the ester-containing organic group (1) contains no olefinic unsaturation and $R^1$ is a linear or branched organic group having from about 2 to about 18 carbon atoms if the ester-containing organic group (1) contains olefinic unsaturation; further wherein $R^2$ is hydrogen or an organic radical of from 1 to about 6 carbon atoms; $R^3$ is a linear unsaturated organic radical of from 1 to about 23 carbon atoms, a linear saturated organic radical of from 1 to about 17 carbon atoms, or a branched organic radical of from about 1 to about 35 carbon atoms; and $R^4$ is a linear or branched organic radical having 0 to about 6 carbon atoms;

(2)

(III)

wherein $R^5$ is a linear or branched organic group having from 2 to about 15 carbon atoms if the ester-containing organic group (2) contains no olefinic unsaturation and $R^5$ is a linear or branched organic group having from 2 to about 23 carbon atoms if the ester-containing organic group (2) contains olefinic unsaturation; further wherein $R^6$ is hydrogen or a linear or branched organic radical of from 1 to about 6 carbon atoms, and $R^7$ is a linear unsaturated organic radical of from 1 to about 23 carbon atoms, a linear saturated organic radical of from 1 to about 17 carbon atoms, or a branched organic radical of from 1 to about 35 carbon atoms; and $R^8$ is hydrogen or a linear or branched organic group having from 1 to about 6 carbon atoms;

(3)

(IV)

wherein $R^9$ is a linear or branched organic group having from 2 to about 14 carbon atoms if the ester-containing organic group (3) contains no olefinic unsaturation and $R^9$ is a linear or branched organic group having from 2 to about 24 carbon atoms if the ester-containing organic group (3) contains olefinic unsaturation; $R^{10}$ is a linear unsaturated organic radical of from 1 to about 22 carbon atoms, a linear saturated organic radical of from 1 to about 14 carbon atoms, or a branched organic radical of from 1 to about 34 carbon atoms; $R^{11}$ is hydrogen or a linear or branched organic radical of from 1 to about 6 carbon atoms; and $R^{12}$ is hydrogen or a linear or branched organic radical of from 1 to about 6 carbon atoms; or (4) chemical reaction mixtures of (1), (2), and (3); or (B) $R^{13}{}_x R^E{}_y SiO_{\frac{1}{2}}$ units and $SiO_{4/2}$ units;

wherein each $R^{13}$ is independently an organic radical, x is a number ranging from 0 to 3, y is a number ranging from 0 to 3, x+y is 3, with the proviso that there is present at least one $R^E$ radical; the ratio of $R^{13}{}_x R^E{}_y SiO_{\frac{1}{2}}$ units to $SiO_{4/2}$ units being from about 0.5:1 to about 4:1.

2. A composition according to claim 1 wherein the liquid silicone ester has a freezing point of up to about 25° C.

3. A composition according to claim 1 wherein R is an alkyl radical, an aryl radical, an aralkyl radical, or any of the foregoing radicals wherein one or more hydrogen atoms is replaced with a halogen, a cyano radical, or an amino radical.

4. A composition according to claim 4 wherein R is methyl or a mixture of methyl and phenyl.

5. A composition according to claim 1 wherein $R^1$, $R^5$, and $R^9$ are independently linear or branched alkyl groups having from about 2 to about 12 carbon atoms if the ester-containing organic groups of (A)(1), (A)(2), and (A)(3), respectively, contain no olefinic unsaturation and $R^1$, $R^5$, and $R^9$ are independently linear or branched organic groups having from about 2 to about 16 carbon atoms if the ester-containing organic groups of (A)(1), (A)(2), and (A)(3), respectively, contains olefinic unsaturation.

6. A composition according to claim 5 wherein $R^1$, $R^5$, and $R^9$ are independently linear or branched alkylene groups having from about 3 to about 10 carbon atoms if the ester-containing organic groups of (A)(1), (A)(2), and (A)(3), respectively, contain no olefinic unsaturation and $R^1$, $R^5$, and $R^9$ are independently linear or branched alkylene groups having from about 3 to about 10 carbon atoms if the ester-containing organic groups of (A)(1), (A)(2), and (A)(3), respectively, contains olefinic unsaturation.

7. A composition according to claim 1 wherein $R^2$ is hydrogen or a linear or branched alkyl group having from 1 to about 5 carbon atoms; $R^3$ is a linear or branched alkyl group having from 8 to about 25 carbon atoms; $R^4$ is a linear or branched alkyl group having from 1 to about 5 carbon atoms; $R^6$ is hydrogen or a linear or branched alkyl group having from about 1 to about 5 carbon atoms; $R^7$ is a linear or branched alkyl group having from about 8 to about 25 carbon atoms; $R^8$ is hydrogen or a linear or branched alkyl group having from about 1 to about 5 carbon atoms; $R^{10}$ is a linear or branched alkyl group, having from about 8 to about 25 carbon atoms; and $R^{11}$ is hydrogen or a linear or branched alkyl group having from about 1 to about 5 carbon atoms; $R^{12}$ is hydrogen or a linear or branched alkyl group having from about 1 to about 5 carbon atoms.

8. A composition according to claim 7 wherein $R^2$ is hydrogen or a linear or branched alkyl group having from 1 to about 3 carbon atoms; $R^3$ is a linear or branched alkyl group, having from 11 to about 17 carbon atoms; $R^4$ is a linear or branched alkyl group having from 1 to about 3 carbon atoms; $R^6$ is hydrogen or a linear or branched alkyl group having from about 1 to about 3 carbon atoms; $R^7$ is a linear or branched alkyl group having from about 11 to about 17 carbon atoms; $R^8$ is hydrogen or a linear or branched alkyl group having from about 1 to about 3 carbon atoms; $R^{10}$ is a linear or branched alkyl group having from about 10 to about 16 carbon atoms; and $R^{11}$ is hydrogen or a linear or branched alkyl group having from about 1 to about 3 carbon atoms; and $R^{12}$ is hydrogen or a linear or branched alkyl group having from about 1 to about 3 carbon atoms.

9. A composition according to claim 1 wherein c is 1, d is 1, and e is 2.

10. A composition according to claim 1 wherein the ratio of $R^{13}{}_x R^E{}_y SiO_{\frac{1}{2}}$ units to $SiO_{4/2}$ units being from about 1:1 to about 3:1.

11. A silicone-water emulsion composition selected from:
   (i) silicone-water emulsions comprising by weight:
      (a) from about 10 to about 70 parts of the liquid silicone ester composition of claim 1;
      (b) from about 0.25 to about 10 parts of an emulsifier; and
      (c) from about 20 to about 89.75 parts of water as a dispersed phase, wherein the sum of (a), (b) and (c) is 100 parts; or
   (ii) silicone-water emulsions comprising by weight:
      (a) from about 0.1 to about 60 parts of the liquid silicone ester composition of claim 1;
      (b) from about 0.25 to about 10 parts of an emulsifier; and
      (c) from about 30 to about 99.65 parts of water as a dispersed phase, wherein the sum of (a), (b), and (c) is 100 parts.

12. A composition according to claim 11 further comprising (d) an effective amount of a personal care agent or a textile softening agent.

13. A method for improving the substantivity, water resistance, workability, emollient properties, payout, and solubility in organic compounds of a personal care or textile softening composition, comprising the step of combining the personal care or textile softening composition with an effective amount of the liquid silicone ester composition of claim 1.

14. An article comprising a substrate coated with the liquid silicone ester composition of claim 1.

15. An article according to claim 14 wherein the substrate is skin, hair, plastic, or textile material.

* * * * *